United States Patent
Lambeau et al.

(10) Patent No.: US 10,670,597 B2
(45) Date of Patent: Jun. 2, 2020

(54) METHODS AND KITS FOR MONITORING MEMBRANOUS NEPHROPATHY

(71) Applicant: EUROIMMUN Medizinische Labordiagnostika AG, Luebeck (DE)

(72) Inventors: Gerard Lambeau, Cabris (FR); Nicola M. Tomas, Hamburg (DE); Barbara Seitz-Polski, La Trinite (FR); Rolf A. K. Stahl, Hamburg (DE)

(73) Assignee: EUROIMMUN Medizinische Labordiagnostika AG, Luebeck (GB)

( * ) Notice: Subject to any disclaimer, the term of this patent is extended or adjusted under 35 U.S.C. 154(b) by 63 days.

(21) Appl. No.: 16/106,141

(22) Filed: Aug. 21, 2018

(65) Prior Publication Data

US 2018/0356417 A1  Dec. 13, 2018

Related U.S. Application Data

(63) Continuation of application No. 15/328,563, filed as application No. PCT/EP2015/066881 on Jul. 23, 2015, now Pat. No. 10,107,810.

(30) Foreign Application Priority Data

Jul. 24, 2014 (EP) .................................. 14306195

(51) Int. Cl.
  *G01N 33/564* (2006.01)
  *G01N 33/68* (2006.01)
  *A61K 38/17* (2006.01)

(52) U.S. Cl.
  CPC ....... *G01N 33/564* (2013.01); *A61K 38/1709* (2013.01); *G01N 33/6893* (2013.01); *G01N 2800/347* (2013.01); *G01N 2800/52* (2013.01)

(58) Field of Classification Search
  None
  See application file for complete search history.

(56) References Cited

U.S. PATENT DOCUMENTS

| 2003/0207348 A1 | 11/2003 | Shimkets et al. |
| 2011/0177534 A1 | 7/2011 | Salant et al. |
| 2013/0280738 A1 | 10/2013 | Salant et al. |

FOREIGN PATENT DOCUMENTS

| WO | 2001/053312 A1 | 7/2001 |
| WO | 2006/110593 | 10/2006 |

OTHER PUBLICATIONS

European Office Action dated Feb. 4, 2019 in European Application No. 15 742 002.7.
Japanese Office Action dated Mar. 12, 2019 in Japanese Application No. 2017-503580 with English translation, 7 pages.
Chieh-Huei Wang, et al., "Thronthospondin Type I Domain Containing 7A (THSD7A) Mediates Endothelial Cell Migration and Tube Formation," Journal of Cellular Physiology, vol. 222, XP055160843, Jan. 1, 2009, pp. 685-694.
Marco Prunotto, et al., "Autoimmunity in Membranous Nephropathy Targets Aldose Reductase and SOD2," Journal of the American Society of Nephrology, vol. 21, No. 3, XP055160848, pp. 507-519, Feb. 11, 2010.
Maurizio Bruschi, et al., "Direct characterization of target podocyte antigens and auto-antibodies in human membranous glomerulonephritis: Alfa-enolase and borderline antigens," Journal of Proteomics, vol. 74, No. 10, XP028272518, May 10, 2011, pp. 2008-2017.
Nicola M. Tomas, et al., "Thrombospondin Type-1 Domain-Containing 7A in Idiopathic Membranous Nephropathy," The New England Journal of Medicine, vol. 371, No. 24, XP009181856, Nov. 13, 2014, pp. 2277-2287.
International Search Report dated Sep. 25, 2015 in PCT/EP2015/066881.
International Preliminary Report on Patentability and Written Opinion dated Jan. 24, 2017 in PCT/EP2015/066881.
Search Report dated Jan. 20, 2015 in European Patent Application No. 14306195.0.
Office Action dated Oct. 24, 2019 in Japanese Application 2017-503580 with English translation (5 pages).
Office Action dated Aug. 23, 2019 in European Application No. 15 742 002.7, 62 pages.
Office Action dated Sep. 12, 2019 in European Application No. 15 742 002.7, 62 pages.

*Primary Examiner* — Daniel C Gamett
(74) *Attorney, Agent, or Firm* — Grüneberg and Myers PLLC

(57) ABSTRACT

An in vitro method can diagnose membranous nephropathy patient. The method includes detecting in a biological sample obtained from the patient one or more autoantibodies recognizing a Thrombospondin, Type I. Domain Containing 7A (THSD7A) protein.

11 Claims, 3 Drawing Sheets

A. Reactivity with a glomerular protein of 250 kDa in size

B. Patient

A. Western blot with recombinant THSD7A

B. Immunoprecipitation (IP)

METHODS AND KITS FOR MONITORING MEMBRANOUS NEPHROPATHY

This application is a continuation of U.S. Pat. No. 15/328,563, filed on Jan. 24, 2017, which is a National Stage entry under § 371 of International Application No. PCT/EP2015/066881, filed on Jul. 23, 2015, and claims priority to European Patent Application No. 14306195.0, filed on Jul. 24, 2014.

FIELD OF THE INVENTION

The present invention relates to a biomarker autoantigen that is specifically recognized by autoantibodies present in a biological sample of patients with membranous nephropathy, particularly idiopathic membranous nephropathy.

The invention provides methods and kits for diagnosing, prognosing, monitoring and treating membranous nephropathy, particularly idiopathic membranous nephropathy in a patient.

BACKGROUND OF THE INVENTION

Membranous nephropathy is a common cause of nephrotic syndrome. About 15% of membranous nephropathy cases are secondary membranous nephropathy, caused by drugs, infections, tumors, immune diseases . . . The remaining 85% of membranous nephropathy cases are idiopathic, also called autoimmune primary membranous nephropathy. Its origin remains unknown. About one half of patients with idiopathic membranous nephropathy who did not receive treatments will develop end-stage renal disease requiring dialysis or renal transplantation. Among the kidney transplants, about 40% of them will relapse.

PLA2R1 has been described as a major autoantigen in idiopathic membranous nephropathy and can be used for the diagnosis and monitoring of treatment of idiopathic membranous nephropathy both before and after kidney graft. Possible therapeutic strategies based on this autoantigen have also been reported.

However, only about 70% of patients suffering from idiopathic membranous nephropathy have anti-PLA2R1 autoantibodies, suggesting that other autoantigens and corresponding autoantibodies may be involved in the remaining 30% cases. Thus, there is a corresponding need for diagnosis, prognosis and theragnosis for the 30% of patients who cannot be followed based on the PLA2RT autoantigen.

SUMMARY OF THE INVENTION

The invention relates to the identification of *Thrombospondin Type I Domain Containing* 7A (THSD7A) as a novel autoantigen in membranous nephropathy and a corresponding in vitro method for diagnosing and/or prognosing membranous nephropathy, particularly idiopathic membranous nephropathy, in a patient, said method comprising the step of detecting in a biological sample obtained from said patient one or more autoantibodies recognizing the THSD7A protein.

In one embodiment, said in vitro method comprises the steps of:
 (i) Contacting a biological sample obtained from said patient with a THSD7A polypeptide or an antibody-binding fragment thereof, and
 (ii) Detecting any antigen-antibody complex formed, wherein the presence of an antigen-antibody complex is indicative of membranous nephropathy.

Preferably, the biological sample is a blood sample.

The invention relates to an in vitro method for assessing the effectiveness of a treatment for membranous nephropathy, particularly idiopathic membranous nephropathy, in a patient, comprising:
 (i) determining at a first time point a level of anti-THSD7A autoantibodies in said sample obtained from said patient at said first time point,
 (ii) determining at a second time point a level of anti-THSD7A autoantibodies in said sample obtained from said patient at said second time point, and
 (iii) comparing the levels of autoantibodies of the two time points, wherein:
  a decrease in the level of anti-THSD7A autoantibodies in the second time point compared to the first time point indicates that the treatment is effective, and/or
  an increase in the level of anti-THSD7A autoantibodies in the second time point compared to the first time point indicates that the treatment is not effective.

The present invention further provides a kit for diagnosing and/or prognosing membranous nephropathy in a patient, said kit comprising:
 a THSD7A polypeptide or an antibody-binding fragment thereof, and
 a reagent for detection of an antigen-antibody complex formed between an autoantigen and an autoantibody present in the biological sample.

The invention also relates to an in vitro method for diagnosing and/or prognosing membranous nephropathy, particularly idiopathic membranous nephropathy, in a patient, comprising the step of determining the THSD7A level in a biological sample obtained from said patient.

In one embodiment, said method comprising the following steps of:
 (i) measuring the level of THSD7A protein in a biological sample obtained from said patient,
 (ii) comparing said level to a reference level,
wherein an increased level of THSD7A protein compared to said reference level is indicative of a membranous nephropathy.

Preferably, the biological sample is a kidney biopsy or a blood sample.

Finally, the invention relates to therapeutic methods, pharmaceuticals compositions and uses for treating membranous nephropathy.

Indeed, the invention relates to a method for treating a membranous nephropathy, particularly idiopathic membranous nephropathy in a patient, the method comprising removing anti-THSD7A autoantibodies from a sample in said patient ex vivo.

The invention also elates to a method for treating a membranous nephropathy, particularly idiopathic membranous nephropathy in a patient, the method comprising administering a therapeutically effective amount of a THSD7A polypeptide or a fragment thereof, a vector expressing said THSD7A polypeptide or a fragment thereof or a host cell expressing said THSD7A polypeptide or a fragment thereof.

Moreover, the invention relates to a THSD7A polypeptide or a fragment thereof (a vector expressing said THSD7A polypeptide or a fragment thereof or a host cell expressing said THSD7A polypeptide or a fragment thereof) for use in the treatment of membranous nephropathy and a pharmaceutical composition comprising said THSD7A polypeptide or a fragment thereof (a vector expressing said THSD7A polypeptide or a fragment thereof or a host cell expressing said THSD7A polypeptide or a fragment thereof), particularly for the treatment of membranous nephropathy, more particularly idiopathic membranous nephropathy.

Preferably, for therapeutic, methods, pharmaceuticals compositions and uses of the invention, the patient is a THSD7A-positive patient.

DETAILED DESCRIPTION OF THE INVENTION

Figure 1:
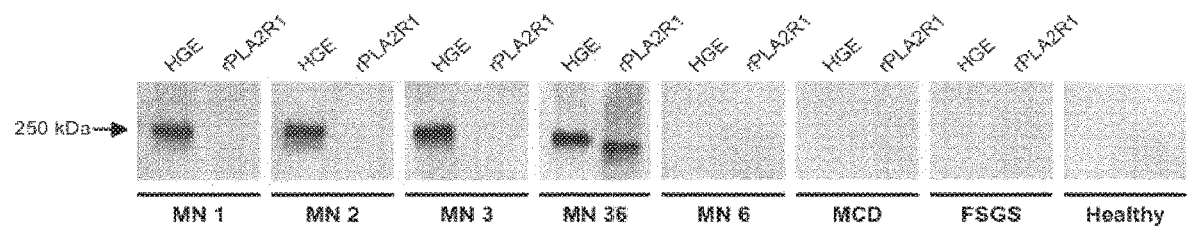
FIG. 1: Detection of autoantibodies against an unknown antigen in patients with membranous nephropathy. A. Results of western blotting on a human glomerular extract (HGE) probed with sera from patients with membranous nephropathy (MN) and from control patients. The majority of these tested patients (88%) was taken from a preexisting serum bank from Hamburg, while the remaining sera were from a cohort of patients from Nice. This panel shows representative images of different reactivity patterns: Three of the depicted MN sera (MN 2 to MN 4) reacted with a glomerular protein of approximately 250 kDa in size, hut not with the recombinant phospholipase A2 receptor (rPLA2R1). One MN serum recognized a glomerular protein of around 180 kDa as well as the recombinant PLA2R1 (MN 36). No reactivity is seen for one MN serum (MN 6), two sera from proteinuric controls, one with minimal change disease (MCD) and one with focal-segmental glomerulosclerosis (FSGS), and one healthy donor. B. Out of sixty-nine patients with membranous nephropathy (MN) who were negative for anti-PLA2R1 antibodies, six reacted with a 250 kDa antigen. Five of these six had idiopathic MN, while one had secondary MN with positive antinuclear antibodies (ANA). No reactivity was seen in anti-PLA2R11 positive patients (n=60), patients with other glomerular diseases (n=76) or healthy controls (n=44).
Figure 1:
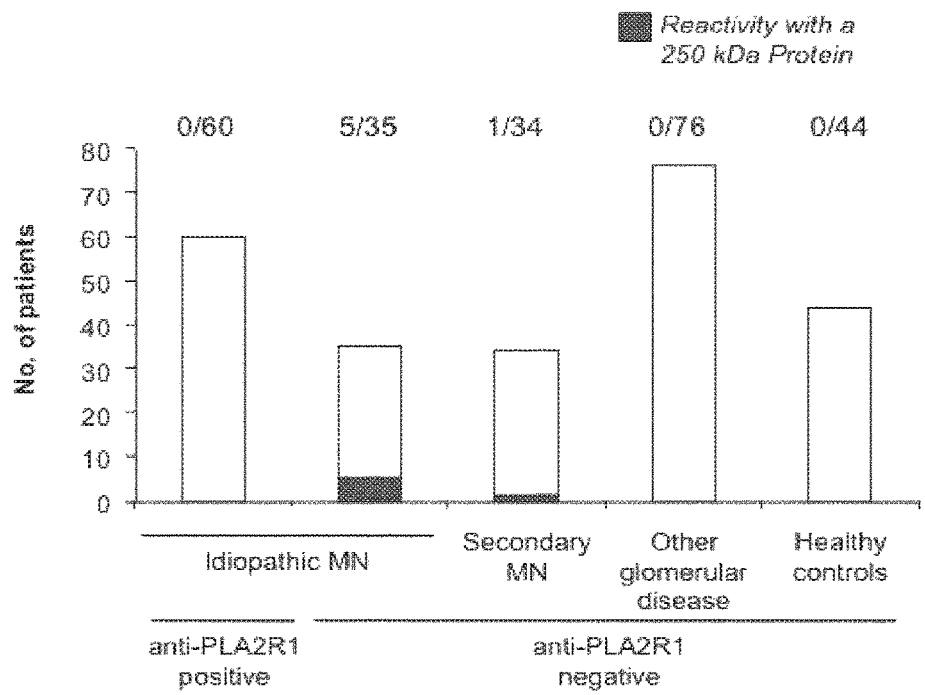

The inventors highlighted the presence of autoantibodies in patients suffering from idiopathic membranous nephropathy that are reactive to a new autoantigen, the *Thrombospondin Type I Domain Containing* 7A (THSD7A) protein.

These autoantibodies are present in sera of about 15% of patients suffering from idiopathic membranous nephropathy that do not present anti-PLA2R1 autoantibodies. That represents about 5-10% of the total population of patients suffering from membranous nephropathy.

The inventors showed that the majority of anti-THSD7A autoantibodies found in patients are of the 404 subclass; subclasses IgG, IgG2, and IgG1 are also found.

Definitions

The term "membranous nephropathy" has its general meaning in the art and refers to a renal disease which is a frequent cause of adult nephrotic syndrome. It encompasses secondary membranous nephropathies that are caused by secondary factors such as systemic lupus erythematosus, hepatitis B, or syphilis ( . . . ), and primary autoimmune membranous nephropathy, also called "idiopathic membranous nephropathy. "Idiopathic membranous nephropathy" is considered to be an autoimmune disease targeting the glomerulus, the major known target antigen being the autoantigen PLA2R1.

All diseases, disorders and symptoms disclosed herein have the general meaning accepted in the art, as evidenced by textbooks, at the time of the filing of the present application.

As used herein, the term "indicative of membranous nephropathy", when applied to a process or event, refers to a process or event which is a diagnostic of membranous nephropathy, such that the process or event is found significantly more often in patients afflicted with membranous nephropathy than in healthy subjects and/or in patients suffering from a disease other than membranous nephropathy.

The terms "biomarker" and "marker" are used herein interchangeably. They refer to a substance that is a distinctive indicator of a biological process, biological event, and/or pathologic condition. According to the invention, the THSD7A protein (or a THSD7A polypeptide) and any antibody-binding fragment thereof and anti-THSD7A autoantibodies are biomarkers of membranous nephropathy, particularly idiopathic membranous nephropathy.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, phosphorylation, citrullination or transglutamination. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as N- or C-terminal added protein tags, glycosyl units, lipids, or inorganic ions such as phosphates, as well as modifications relating to chemical conversion of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

Figure 4:
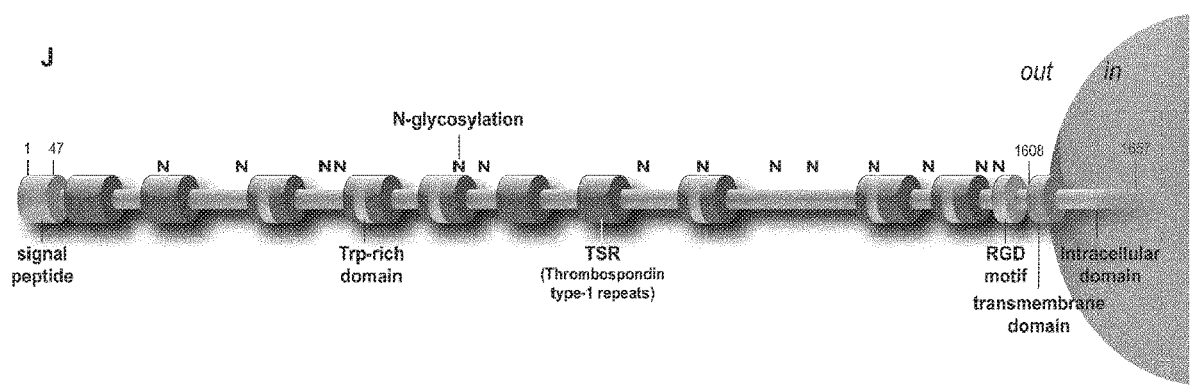
FIG. 4: Molecular architecture of the large THSD7A protein (1657 amino acids). The TSHD7A protein consists of a large extracellular part containing a signal peptide, at least ten thrombospondin type 1 repeats (several of which contain tryptophan-rich sequences) and one RGD motif, a transmembrane domain starting at the amino acid residue 1608 and a short intracellular tail.

The term THSD7A (*Thrombospondin Type I Domain Containing* 7A) has its general meaning in the art and refers to a protein of 1657 amino acids highly expressed on podocytes and involved in endothelial cell migration and filopodia formation during angiogenesis via a FAK-dependent mechanism. The term may include naturally occurring THSD7A and variants and modified forms thereof. THSD7A may be from any source, but typically is a mammalian (e.g., human and non-human primate or other mammalian species) THSD7A, particularly a human THSD7A. An exemplary human native THSD7A amino acid sequence is provided in Q9UPZ6 (UniProt database) and NP_056019 (GenPept database, precursor sequence) and an exemplary human native THSD7A mRNA sequence is provided in NM_015204 (GenBank database, precursor sequence). The structure of THSD7A protein is illustrated in FIG. 4.

As used herein, the expression "fragment of THSD7A" refers to a continuous element of THSD7A. Typically, said fragment is a biologically active fragment, i.e it comprises one or more functional properties of THSD7A.

In the context of the present invention, a "fragment" of THSD7A comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire amino acid sequence of THSD7A.

Preferably, said fragment comprises at least 100, at least 200, at least 300, at least 400, at least 500, at least 600, at least 700, at least 800, at least 900, at least 1000, at least 1100, at least 1120, at least 1250, at least 1300, at least 1400, at least 1500, at least 1600, at least 1620, at least 1640 amino acids of the entire amino acid sequence of THSD7A.

Preferably, said fragment is recognized by an autoantibody directed against THSD7A. Determining the ability of the fragment to interact with said autoantibodies can be accomplished by one of the methods described above or known in the art for determining direct binding.

The term PLA2R1 (secretory phospholipase A2 receptor, also known as PLA2R1) has its general meaning in the art and herein refers to the M-type phospholipase A2 receptor, a receptor encoded in humans by the PLA2R1 gene, particularly known as a. major antigen in idiopathic membranous nephropathy, An exemplary human native PLA2R1 amino acid sequence is provided in NP_001007268 (GenPept database) and an exemplary human native THSD7A mRN A sequence is provided in NM_001007267 (GenBank database). It is noteworthy that all reference to database such as codes or accession numbers disclosed herein refer to the versions available online on Jul. 24, 2014.

The term "PLA2R1-negative patient" or "THSD7A-negative patient" refers to a patient whose serum contains no autoantibodies (or at least no detectable autoantibodies) directed against PLA2R1 or THSD7A, respectively, Conversely, "PLA2R1-positive patient" or "THSD7A-positive patient" refers to a patient whose serum contains autoantibodies directed against PLA2R1 or THSD7A respectively.

The term "autoantibody" has its general meaning in the art and refers to an antibody that is produced by the immune system of a subject (or patient) and that is directed against subject's (or patient's) own proteins (for example THSD7A). Autoantibodies may attack the body's own cells, tissues, and/or organs, causing inflammation and cell injury. The terms "autoantibody recognizing THSD7A" can be used interchangeably with "anti-THSD7A autoantibody".

The term "antibody-binding fragment", when used herein in connection with an antigen (e.g. THSD7A), refers to a fragment of the antigen that retains the ability of the antigen to bind an antibody to form an antibody-antigen complex. In particular, an antibody-binding fragment of an antigen of the present invention retains the ability to bind autoantibodies specific to membranous nephropathy. Suitable antibody-binding fragments of an antigen may be identified by one skilled in the art by simple trials to ascertain their ability to bind specific autoantibodies of membranous nephropathy.

As used herein, the term "patient" refers to a human subject or another mammal subject (e.g., primate, dog, cat, goat, horse, pig, mouse, rat, rabbit, and the liked), that can be afflicted with a membranous nephropathy, particularly an idiopathic membranous nephropathy. Preferably, the patient is a human patient. More preferably, said patient is suspected to be afflicted with a membranous nephropathy, particularly an idiopathic membranous nephropathy.

The term "biological sample" is used herein in its broadest sense. A biological sample is generally obtained for a subject. Said subject is mammal, preferably human. Typically, biological sample is generally obtained from a patient. Typically, said sample comprises a representative set of autoantibodies.

A sample may be of any biological tissue or fluid with which biomarker(s) of the present invention may be assayed. Such samples include, but are not limited to, bodily fluids which may or may not contain cells, e.g., blood (e.g., whole blood, serum or plasma). Such samples also include biopsies (for example kidney biopsy). The term biological sample also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like.

In the context of the present invention, the term "control", when used to characterize a subject, refers to a subject that is healthy or to a patient that has been diagnosed with a specific disease other than renal disease. The term "control sample" refers to one, or more than one sample, that has been obtained from a healthy subject or from a patient diagnosed with a disease other than renal disorder.

The terms "normal" and "healthy" are used herein interchangeably. They refer to a subject that has not shown any symptom associated with renal disorder, and that has not been diagnosed with membranous nephropathy or other nephropathy. Preferably, a normal subject is not on medication affecting renal system and has not been diagnosed with any other disease. In certain embodiments, normal subjects have similar sex, age, and/or body mass index as compared with the subject from which the biological sample to be tested was obtained. The term "normal" is also used herein to qualify a sample obtained from a healthy subject.

As used herein, the term "reference level" refers to a level measured in a biological sample obtained from a control or preferably to an average of several levels measured in biological samples obtained from several controls.

As used herein, the term "diagnosis", "diagnosing" or "diagnostic" is used on its broadest sense and encompasses diagnosis, prognosis, theragnosis and monitoring in membranous nephropathy.

As used herein, the term "treat" or treatment" refers to reducing or alleviating at least one adverse effect or symptom associated with medical conditions that are associated with membranous nephropathy, particularly idiopathic membranous nephropathy. These include reducing the amount of anti-THSD7A autoantibodies, reducing, inhibiting or stopping the production of anti-THSD7A autoantibodies, suppression of the immune system, and reducing the inflammation and degradation/damage associated with the activities of the autoantibodies when they are bound to the kidney glomeruli.

As used herein, the term "theragnosis" refers to the identification, for example by diagnostic methods, of patients who might benefit from a particular therapy.

As used herein, the term "therapeutically effective amount" refers to that amount of active agent that can reduce the amount of soluble anti-THSD7A autoantibodies. The amount reduction is at least 10%, particularly at least 20%, more particularly at least 40%, preferably at least 60%, more preferably at least 80%, even more preferably at least 95%, reduction in the autoantibodies compared to the amount of autoantibodies present in the serum prior to the start of a treatment.

As used herein, the term "pharmaceutical composition" refers to the active agent of the invention (e.g. a THSD7A polypeptide or a fragment thereof, a vector expressing said THSD7A polypeptide or a fragment thereof, or a host cell expressing said THSD7A polypeptide or a fragment thereof, as described below) in combination with a pharmaceutically acceptable carrier of chemicals and compounds commonly used in the pharmaceutical industry.

Diagnostic and Prognostic Methods and Kits Based on Detection of Anti-THSD7A Autoantibodies
Diagnostic Methods Thus, a first object of the invention relates to an in vitro method for diagnosing and/or prognosing membranous nephropathy, more particularly idiopathic membranous nephropathy, in a patient, said method comprising the step of detecting in a biological sample obtained from said patient one or more autoantibodies recognizing the THSD7A protein.

In a preferred embodiment, the biological sample is a blood sample (including whole blood, serum or plasma). Preferably, the biological sample is serum or plasma.

In one embodiment, the in vitro method for diagnosing and/or prognosing a membranous nephropathy, particularly idiopathic membranous nephropathy, in a patient, comprises the steps of:
  (i) Contacting a biological sample obtained from said patient with a THSD7A polypeptide or an antibody-binding fragment thereof, and
  (ii) Detecting any antigen-antibody complex formed, wherein the presence of an antigen-antibody complex is indicative of membranous nephropathy.

In one embodiment of the invention, the THSD7A polypeptide or an antibody-binding fragment thereof may be from different mammalian species, particularly human, non-human primate, pig, rabbit, or mouse.

In one embodiment, the THSD7A polypeptide may be a full THSD7A protein.

In one embodiment of the invention, an antibody-binding fragment may comprise or consist of the full extracellular domain of THSD7A or a fragment thereof constituted by one or several of its distinct thrombospondin type I domains and/or linker stalks of THSD7A.

The THSD7A polypeptides and more generally all biomarkers of the present invention may be prepared by any suitable method, including recombinant methods. Such methods, as described, for example, in "The Proteins" (Vol. II, 3rd Ed., H. Neurath et al. (Eds.), 1976, Academic Press: New York, NY, pp. 105-237) may also be used to synthesize the biomarkers of the invention.

In certain embodiments, a polypeptide/protein biomarker of the invention (e.g. THSD7A polypeptide) is immobilized onto a solid carrier or support (e.g., a bead or array). Therefore, in this embodiment, the method of the invention involves the use of a device coated with the THSD7A polypeptide or a fragment thereof. Typically, said device is a medical device or a diagnostic device, preferably a diagnostic device.

Typically, in the context of the invention the THSD7A polypeptide or a fragment thereof is immobilized onto said device.

The diagnostic methods of the present invention involve detection of an antigen antibody complex formed between the biomarker of the invention (e.g. THSD7A polypeptide) and an autoantibody present in the biological sample tested. This detection is indicative of the presence of autoantibodies (namely anti-THSD7A autoantibodies)) in said sample.

In the practice of the invention, detection of such a complex may be performed by any suitable method (see, for example, E. Harlow and A. Lane, "Antibodies: A Laboratories Manual", 1988, Cold Spring Harbor Laboratory: Cold Spring Harbor, N.Y.).

For example, detection of an antigen-antibody complex may be performed using an immunoassay, A wide range of immunoassay techniques is available, including radioimmunoassay, enzyme immunoassays (EIA), enzyme-linked immunosorbent assays (ELBA), immunofluorescence immunoprecipitation, and line blot. Immunoassays are well known in the art and falls within the general knowledge of the person skilled in the art. Methods for carrying out such assays as well as practical applications and procedures are summarized in textbooks. Examples of such textbooks include P. Tijssen, In: Practice and theory of enzyme immunoassays, eds. R. H. Burdon and v. P. H. Knippenberg, Elsevier, Amsterdam (1990). pp. 221-278 and various volumes of Methods in Enzymology, Eds. S. P. Colowick et al, Academic Press, dealing with immunological detection methods, especially volumes 70, 73, 74, 84, 92 and 1121. Immunoassays may be competitive or non-competitive. For example, any of a number of variations of the sandwich assay technique may be used to perform an immunoassay. Briefly, in a typical sandwich assay applied to the detection of anti-THSD7A autoantibodies according to the present invention, an unlabeled THSD7A polypeptide (biomarker) is immobilized on a solid surface (as described above) and the biological sample to be tested is brought into contact with the bound biomarker for a time and under conditions allowing formation of an antigen-antibody complex. Preferably, the formation of antigen-antibody complex is done under non-reducing conditions.

Following incubation, an antibody that is labeled with a detectable moiety and that specifically recognizes antibodies from the species tested (e.g., an anti-human IgG for human subjects) is added and incubated under conditions allowing the formation of a ternary complex between any biomarker-bound autoantibody and the labeled antibody. Any unbound material is washed away, and the presence of any anti-THSD7A autoantibody in the sample is determined by observation/detection of the signal directly or indirectly produced by the detectable moiety. Variations on this assay include an assay, in which both the biological sample and the labeled antibody are added simultaneously to the immobilized THSD7A-protein/polypeptide biomarker.

The second antibody (i.e., the antibody added in a sandwich assay as described above) may be labeled with any detectable moiety, i.e., any entity which, by its chemical nature, provides an analytically identifiable signal allowing detection of the ternary complex, and consequently detection of the biomarker-antibody complex.

Detection may be either qualitative or quantitative. Methods for labeling biological molecules such as antibodies are well-known in the art (see, for example, "Affinity Techniques. Enzyme Purification: Part B", Methods in Enzymol, 1974, Vol. 34, W. H. Jakoby and M. Wilneck (Eds.), Academic Press: New York, N.Y.; and M. Wilchek and E. A. Bayer, Anal. Biochem., 1988, 171: 1-32). The most commonly used detectable moieties in immunoassays are enzymes and fluorophores. In the case of an enzyme immunoassay (EIA or ELISA), an enzyme such as horseradish perodixase, glucose oxidase, beta-galactosidase, alkaline phosphatase, and the like, is conjugated to the second antibody, generally by means of glutaraldehyde or periodate. The substrates to be used with the specific enzymes are generally chosen for the production of a detectable color change, upon hydrolysis of the corresponding enzyme. In the case of immunofluorescence, the second antibody is chemically coupled to a fluorescent moiety without alteration of its binding capacity. After binding of the fluorescently labeled antibody to the biomarker-antibody complex and removal of any unbound material, the fluorescent signal generated by the fluorescent moiety is detected, and optionally quantified. Alternatively, the second antibody may be labeled with a radioisotope, a chemiluminescent moiety, or a bioluminescent moiety.

Typically, in the context of the invention, the THSD7A polypeptide is an isolated polypeptide or a recombinant polypeptide.

As mentioned above, the biomarkers of the invention are specifically recognized by the sera of a population of patients afflicted with a membranous nephropathy, more specifically an idiopathic membranous nephropathy, and in particular by sera of patients afflicted with a membranous nephropathy who do not have anti-PLA2R1 autoantibodies.

Thus, in a particular embodiment of the invention, said patient is a PLA2R-negative patient.

The patient has also been tested negative for all usual causes of membranous nephropathy, for example, systemic lupus erythematosus, hepatitis B and syphilis.

Currently, there is no non-invasive method available for the diagnosis of membranous nephropathy, particularly idiopathic membranous nephropathy, for PLA2R1-negative patients. Said patients thus have to undergo a kidney biopsy.

Conversely, the method of the invention is highly promising since it could exonerate from the need of performing invasive techniques, in THSD7A negative patients, as well as in THSD7A-positive patients.

In a particular embodiment, said patient did not and/or will not undergo a kidney biopsy.

Said method may also be applied in parallel to the diagnostic method of membranous nephropathy based on the detection of anti-PLA2R1 autoantibodies (described in the patent application WO2010/009457) and additional biomarkers of membranous nephropathy, for example biomarkers of secondary membranous nephropathies, may be assessed. Examples of such biomarkers include, but are not limited to antinuclear antibodies (ANA), anti-hepatitis B antigens and rapid plasma reagin (RPR).

Results obtained using said diagnostic method may be compared to and/or combined with clinical data, results from other tests, assays or procedures performed for the diagnosis of membranous nephropathy. Such comparison and/or combination may help provide a more refine diagnosis.

Prognostic Methods and Monitoring of Treatment of Membranous Nephropathy

The inventors also showed a correlation between the presence and level of anti-THS7A autoantibodies and effectiveness of treatment, remission or relapse of patients with membranous nephropathy, more specifically idiopathic membranous nephropathy.

Current treatments used for membranous nephropathy, particularly idiopathic membranous nephropathy, are immunosuppressive therapy, for example, cyclosporin, tacrolimus, azathioprine, infliximab, omalizumab, daclizumab, adalimumab, eculizumab, efalizumab, natalizumab, omalizumab and rapamycin. It also includes cyclophosphamide, chlorambucil, and rituximab.

Thus, a further object of the invention relates to an in vitro method for assessing the effectiveness of a treatment for membranous nephropathy, particularly idiopathic membranous nephropathy, in a patient, comprising:
  (i) determining at a first time point a level of anti-THSD7A autoantibodies in said sample Obtained from said patient at said first time point,
  (ii) determining at a second time point a level of anti-THSD7A autoantibodies in said sample obtained from said patient at said second time point, and
  (iii) comparing the levels of autoantibodies of the two time points.
wherein:
  a decrease in the level of anti-THSD7A autoantibodies in the second time point compared to the first time point indicates that the treatment is effective, and/or
  an increase in the level of anti-THSD7A autoantibodies in the second time point compared to the first time point indicates that the treatment is not effective.

The method of the invention is preferably performed for patients that have been diagnosed for membranous nephropathy, particularly idiopathic membranous nephropathy and that are THSD7A-positive patients.

In the practice of the invention, determination of the level of anti-THSD7A autoantibodies may be performed by any suitable quantitative method, for example as described above (see, for example, E. Harlow and A. Lane, "Antibodies: A Laboratories Manual", 1988, Cold Spring Harbor Laboratory: Cold Spring Harbor, N.Y.). Particularly, the level of the anti-THSD7A autoantibodies can be detected by an immunoassay wherein an antigen-antibody complex is formed.

As explained above, the patient has typically initially been diagnosed with membranous nephropathy and has a detectable amount of anti-THSD7A autoantibodies. Upon treatment, for example, with immunosuppressive therapy, over time, a decrease in the amount of detectable anti-THSD7A autoantibodies is observed in case of effective treatment.

The treatment is considered to be effective when a decrease of at least 10%, particularly at least 20%, more particularly at least 30%, even more particularly at least 40%, preferably at least 50%, more preferably at least 60%, even more preferably at least 70%, still even more preferably at least 80%, of the level of anti-THSD7A autoantibodies is observed. This generally indicates a good prognosis.

In an ideal case, the amount of autoantibodies should fall below the detectable level of the detection methods described herein and the patient is deemed to be in remission for the disorder.

Conversely, the treatment is considered to be ineffective when level between the first and the second time point is stable or increases by at least 5%, particularly at least 10%, more particularly at least 20%, even more particularly at least 30%, still even more particularly at least 40%, preferably at least 50%, more preferably at least 60%, even more preferably at least 70%, still even more preferably at least 80% or more of the initial level of anti-THSD7A autoantibodies.

Several situations may be observed.

In one embodiment, no anti-THSD7A autoantibodies are detected at the second time point. This indicates that the patient is deemed to be in remission.

In another embodiment, a stable level of anti-THSD7A autoantibodies is observed: the levels obtained at the first and the second time points are comparably similar within statistical analysis variances, with a deviation between about a 1-5% deviation, preferably a 1-3% deviation. This indicates a stable disease wherein the treatment has been of insufficient duration (so it should be continued if clinically indicated) or is non-effective.

In another embodiment, an increased level of anti-THSD7A autoantibodies is observed at the second time point compared to the first time point and the first time point had detectable anti-THSD7A autoantibodies. This indicates a worsening of the disease and/or lack of efficient treatment. An increase of at least 30%, preferably at least 50%, more preferably at least 100%, even more preferably at least 200% is considered to indicate a worsening of the situation and a poor prognosis.

In another embodiment, an increased level of anti-THSD7A autoantibodies is observed at the second time point compared to the first one and the first time point had no detectable anti-THSD7A autoantibodies. This indicates that the patient has relapsed and that the membranous nephropathy has recurred.

According to the invention, the second time point is chosen later than the first time point. The first and second time points may be strategically chosen, for example with regard to the therapeutic strategy and for the follow-up of a patient who is at risk to develop a membranous nephropathy, particularly an idiopathic membranous nephropathy, or who already suffered from a membranous nephropathy, particularly an idiopathic membranous nephropathy, and is at risk to relapse.

For example, the first time point may be before administration of any treatment to the patient and second time point could be placed at a moment when the treatment should show an effect, or at the end of treatment, and the assay may be repeated later.

The assay thus may be reproduced several times; the anti-THSD7A autoantibodies level may be assessed at more than two time points. The comparison of step (iii) has to be done with the first time point or with the previous time point. An improvement of the patient health and an effectiveness of treatment are indicated when a global decrease of anti-THSD7A autoantibodies level is observed during time. Conversely, a degradation of the patient health and an ineffectiveness of treatment are indicated when no decrease of anti-THSD7A autoantibodies level is observed during time, particularly when a global increase is observed. A reappearance of detectable anti-THSD7A autoantibodies after a period of no-detectable anti-THSD7A autoantibodies is indicative of a relapse.

The assay used is identical for all the samples collected from the patient at the different time points.

In a case of ineffective treatment, the therapeutic strategy has to be adapted.

In view of what is described above, the in vitro method for assessing the effectiveness of a treatment for membranous nephropathy, particularly idiopathic membranous nephropathy, in a patient &so constitutes a method for prognosing membranous nephropathy, particularly idiopathic membranous nephropathy, in a patient.

Kits

In another aspect, the present invention provides kits comprising materials useful for carrying out methods according to the present invention. The diagnosis procedures provided herein may be performed by diagnostic laboratories, experimental laboratories, or practitioners. The invention provides kits that can be used in these different settings.

Materials and reagents for detecting THSD7A autoantibodies in a biological sample and/or for diagnosing membranous nephropathy in a patient according to the present invention may be assembled together in a kit. Each kit of the invention comprises at least one protein/polypeptide biomarker of the invention preferably in an amount that is suitable for detection of autoantibodies in a biological sample.

Thus, a further object of the invention relates to a kit for detecting autoantibodies recognizing THSD7A in a biological sample obtained from a patient, said kit comprising:
 a THSD7A polypeptide or an antibody-binding fragment thereof, and
 a reagent for detection of an antigen-antibody complex formed between an autoantigen, preferably a THSD7A polypeptide or an antibody-binding fragment thereof and an autoantibody, preferably an autoantibody directed to against THSD7A present in the biological sample.

According to the invention, the reagent permits to detect an autoantibody present in said biological sample wherein the autoantibody is an anti-THSD7A autoantibody that is indicative of membranous nephropathy.

In the context of the invention, said THSD7A polypeptide is a mammalian THSD7A polypeptide/protein or an antibody-binding fragment thereof, preferably a human THSD7A polypeptide/protein or an antibody-binding fragment thereof, particularly comprising or consisting of the extracellular domain of THSD7A or a fragment thereof constituted by one or several of its distinct thrombospondin type I domains and/or linker stalks.

In one embodiment of the invention, the THSD7A polypeptide or an antibody-binding fragment thereof may be from different mammalian species, particularly from human, non-human primate, pig, rabbit, or mouse.

In one embodiment, the invention relates to a kit of the invention as described above for diagnosing membranous nephropathy in a patient.

In one embodiment, said kit further comprises a PLA2R1 polypeptide or an antibody-binding fragment thereof.

In the context of the invention, said PLA2R1 polypeptide is a mammalian PLA2R1 polypeptide/protein and an antibody-binding fragment thereof, preferably a human PLA2R1 polypeptide/protein and an antibody-binding fragment thereof.

In one embodiment of the invention, the PLA2R1 polypeptide or an antibody-binding fragment thereof may be from different mammalian species, particularly from human, non-human primate, pig, rabbit, or mouse.

The reagent for detection of an antigen-antibody complex formed between the autoantigen marker and an autoantibody present in the biological sample, also permits to detect an anti-PLA2R1 autoantibody that is indicative of membranous nephropathy (further to anti-THSD7A autoantibody).

In another embodiment, said kit may further comprise at least one additional biomarker of membranous nephropathy, for example biomarkers of secondary membranous nephropathies (such as ANA, anti-hepatitis B antigens, rapid plasma reagin . . . ).

The polypeptide biomarker(s) included in a kit of the invention may or may not be immobilized on the substrate surface (e.g., beads, array, and the like).

Thus, in an aspect, the invention further relates to a device coated with the THSD7A polypeptide or a fragment thereof. Typically, said device is a medical device or a diagnostic device, preferably a diagnostic device.

Preferably, said device is used in a method for diagnosing and/or prognosing a membranous nephropathy, particularly idiopathic membranous nephropathy. Typically, in the context of the invention, the THSD7A polypeptide or a fragment thereof is immobilized onto said device.

Methods for immobilizing polypeptide molecules onto a solid surface are known in the art. A polypeptide/protein may be immobilized by being either covalently or passively bound to the surface of a solid carrier or support. Examples of suitable carrier or support materials include, but are not limited to, agarose, cellulose, nitrocellulose, dextran, Sephadex, Sepharose, carboxymethyl cellulose, polyacrylamides, polystyrene, polyvinyl chloride, polypropylene, filter paper, magnetite, ion-exchange resin, glass, polyamine-methyl-vinyl-ether-maleic acid copolymer, amino acid copolymer, ethylene-maleic acid copolymer, nylon, silk, and the like. Immobilization of a polypeptide/protein biomarker on the surface of a solid carrier or support may involve crosslinking, covalent binding or physical adsorption, using methods well known in the art. The solid carrier or support may be in the form of a bead, a particle, a microplate well, an array, a cuvette, a tube, a membrane, or any other shape suitable for conducting a diagnostic method according to the invention (e.g., using an immunoassay).

Thus, in preferred embodiments, a kit of the invention includes an array for diagnosing membranous nephropathy, particularly idiopathic membranous nephropathy, as provided herein. Alternatively, a substrate surface may be included in a kit of the invention for immobilization of the biomarkers of the invention.

A kit of the invention also comprises at least one reagent for the detection of a biomarker-antibody complex formed between the peptide biomarker (for example THSD7A and/or PLA2R) included in the kit and an autoantibody present in a biological sample. Such a reagent may be, for example, a labelled antibody that specifically recognizes antibodies from the species tested (e.g., an anti-human IgG, particularly IgG4, IgG3, IgG2, and IgG1 preferably IgG4, for human subjects), as described above.

In one embodiment, said labelled antibody recognizes all forms of human IgG.

In another embodiment, said labelled antibody particularly recognizes the human IgG4 subclass.

Depending on the procedure, the kit may further comprise one or more of the following: extraction buffer and/or reagents, blocking buffer and/or reagents, immunodetection buffer and/or reagents, labeling buffer and/or reagents, and detection means. Protocols for using these buffers and reagents for performing different steps of the procedure may be included in the kit. The different reagents included in the kit of the invention may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, a kit comprises instructions for using its components for the diagnosis of membranous nephropathy, in particular idiopathic membranous nephropathy, in a patient according to a method of the invention. Instructions for using the kit according to methods of the invention may comprise instructions for processing the biological sample obtained front the patient and/or for performing the test, and/or instructions for interpreting the results. A kit may also contain a notice in the form prescribed by a governmental agency regulating the manufacture, use or sale of pharmaceuticals or biological products.

In a particular embodiment, the invention provides an array or protein array for the diagnosis of membranous nephropathy, particularly idiopathic membranous nephropathy, comprising, immobilized to its surface, at least the THSD7A polypeptide biomarker of the invention. Preferably, the array comprises more than one polypeptide/protein biomarker of the invention and thus also comprises PLA2R1 polypeptide biomarker, suitable for the detection of PLA2R-positive patients. The array may further comprise at least one additional biomarker of membranous nephropathy for example biomarkers of secondary membranous nephropathies (such as ANA, anti-hepatitis B antigens, rapid plasma reagin . . . ).

In another particular embodiment, the present invention also provides a protein bead suspension array for the diagnosis of membranous nephropathy, particularly idiopathic membranous nephropathy. This bead suspension array comprises a suspension of one or more identifiable distinct particles or beads, wherein each bead contains coding features relating to its size, color or fluorescence signature and wherein each bead is coated with a polypeptide/protein biomarker of the present invention.

A still further object of the invention relates to the use of a kit, an array or a bead of the invention for diagnosing membranous nephropathy, in particular idiopathic membranous nephropathy, in a patient.

In one embodiment, said kit, array or bead of the invention comprises
    a THSD7A polypeptide or an antibody-binding fragment thereof, and
    a reagent for detection of an antigen-antibody complex formed between
the autoantigen marker and an autoantibody present in the biological sample, and can be used according to the methods of the invention.

Said kit, array or bead of the invention may also be used for assessing the effectiveness of a treatment for membranous nephropathy, particularly idiopathic membranous nephropathy, in a patient and for prognosing membranous nephropathy, particularly idiopathic membranous nephropathy, in a patient.

In a particular embodiment, said patient has been previously assessed for the presence of autoantibodies recognizing PLA2R1 and is negative for said autoantibodies. The patient has also been tested negative for all usual causes of membranous nephropathy, for example, systemic lupus erythematosus, hepatitis B and syphilis.

in that case, the kit or array of the invention used for diagnosing membranous nephropathy in said patient comprises neither PLA2R1 polypeptide or an antibody-binding fragment thereof nor any other biomarker of membranous nephropathy.

Diagnostic Methods and Kits Based on the Detection of THSD7A Autoantigen

The inventors showed that the autoantigen THSD7A is overexpressed in kidney of patients afflicted with a membranous nephropathy, particularly with an idiopathic membranous nephropathy (particularly in patients having THSD7A autoantibodies).

So, a further object of the invention relates to the use of THSD7A as a biomarker of membranous nephropathy, particularly idiopathic membranous nephropathy.

The invention thus relates to an in vitro method for diagnosing and/or prognosing membranous nephropathy, particularly idiopathic membranous nephropathy in a patient, comprising the step of determining the THSD7A level in a biological sample obtained from said patient.

According to the invention, said in vitro method for diagnosing and/or prognosing membranous nephropathy, particularly idiopathic membranous nephropathy in a patient also encompasses the monitoring of membranous nephropathy, particularly idiopathic membranous nephropathy in a patient.

According to the invention, the THSD7A level encompasses THSD7A protein level and mRNA protein level.

In a particular embodiment, said patient is a PLA2R-negative patient.

In one embodiment, said method may also be applied in parallel to the diagnostic method of membranous nephropathy based on the detection of anti-PLA2R autoantibodies and additional biomarkers of membranous nephropathy, In another embodiment, said biological sample is preferably a blood sample or a kidney biopsy.

Diagnostic Method Based on Detection of THSD7A Protein Level

In one embodiment, the invention relates to an in vitro method for diagnosing and/or prognosing membranous nephropathy, particularly idiopathic membranous nephropathy in a patient, comprising the step of determining the level of THSD7A protein in a biological sample obtained from said patient.

In a particular embodiment, said method comprises the following steps:
  (i) Measuring the level of THSD7A protein in a biological sample obtained from said patient,
  (ii) Comparing said level to a reference level,
wherein an increased level of THSD7A protein compared to said reference level is indicative of a membranous nephropathy, particularly an idiopathic membranous nephropathy.

Preferably, the biological sample is a blood sample or a kidney biopsy.

Typically, an increased level of THSD7A protein corresponds to an increase of at least 20%, preferably at least 50% of the protein level measured in a control sample.

THSD7A level can be measured by different methods well known in the art.

In a particular embodiment, the methods of the invention comprise contacting the biological sample with a binding partner capable of selectively interacting with the biomarkers (e.g. THSD7A) present in the biological sample.

The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated by using any technique that provides the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce single chain antibodies directed against biomarkers of the invention. Antibodies useful in practicing the present invention also include anti-biomarkers fragments including but not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab and/or scFv expression libraries can be constructed to allow rapid identification of fragments having the desired specificity to biomarkers of the invention. For example, phage display of antibodies may be used. In such a method, single-chain Fv (scFv) or Fab fragments are expressed on the surface of a suitable bacteriophage, e. g., M13. Briefly, spleen cells of a suitable host, e.g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e.g., bacteria, the phage displays the antibody fragment. Phage display of antibodies may also be provided by combinatorial methods known to those skilled in the art. Antibody fragments displayed by a phage may then be used as part of an immunoassay. VHH may also be used.

Examples of commercially available monoclonal antibodies recognizing THSD7A include those obtained from Abcam (ab121122), Novas Biologicals (NBP1-93612), Abnova Corporation (PAB20021), Atlas Antibodies (HPA000923) and Santa Cruz (sc-163453, se-163455).

In another embodiment, the binding partner may be an aptamer. Aptamers are a class of molecules that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention such as antibodies or aptamers may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically slinking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123,I124, InI 11, Re186, Re188.

The aforementioned assays may involve the binding of the binding partner (ie. antibody or aptamer) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., heads or microtiter plates); polyvinylidine fluoride; diazotized paper; nylon membranes; activated beads, magnetically responsive beads, and the like.

Biomarkers of the invention may be detected by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of antibodies directed against biomarkers of the invention. A biological sample containing or suspected of containing said biomarker(s) is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Alternatively an immunohistochemistry (IHC) method may be used. IHC specifically provides a method of detecting targets in a sample or tissue specimen in situ. The overall cellular integrity of the sample is maintained in MC, thus allowing detection of both the presence and location of the targets of interest. Typically, a sample is fixed with formalin, embedded in paraffin and cut into sections for staining and subsequent inspection by light microscopy. Current methods of use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan).

In particular embodiment, a tissue section (i.e. a kidney biopsy sample) may be mounted on a slide or other support after incubation with antibodies recognizing the biomarkers of the invention (e.g. anti-THSD7A antibodies). Then, microscopic inspections in the sample mounted on a suitable solid support may be performed. For the production of photomicrographs, sections comprising samples may be mounted on a glass slide or other planar support, to highlight by selective staining the presence of biomarkers of the invention (e.g. THSD7A protein).

Therefore, IHC samples may include, for instance: (a) preparations comprising fresh tissues or cells isolated form said tissues (b) fixed and embedded said tissue or cells samples and (c) detecting biomarkers of the invention THSD7A protein) in said tissues or cells samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibody recognizing the biomarkers of the invention, washing, applying secondary antibody (optionally coupled to a suitable detectable label), washing, counter staining, and microscopic examination.

Detecting the biomarker(s) (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, biomarkers of the invention may be identified based on the known "separation profile" e. g., retention time, for that compound and measured using standard techniques.

Alternatively, the separated compounds may be detected and measured by, for example, a mass spectrometer, especially when fragments or peptides of the biomarker(s) are measured.

In another aspect, as described above, the present invention provides kits comprising materials useful for carrying out methods according to the present invention. The diagnosis procedures provided herein may be performed by diagnostic laboratories, experimental laboratories, or practitioners. The invention provides kits that can be used in these different settings.

Materials and reagents for detecting THSD7A level (at mRNA or protein level) in a biological sample and/or for diagnosing membranous nephropathy in a patient according to the present invention may be assembled together in a kit.

In one embodiment, a kit of the invention comprises at least an antibody recognizing THSD7A or other binding partner of THSD7A.

In a particular embodiment, said kit may further comprise at least an antibody recognizing PLA2R1 or other binding partner of PLA2R1.

In another particular embodiment, said kit may also comprise at least one another antibody (or another binding partner) recognizing another biomarker of membranous nephropathy, for example biomarkers of secondary membranous nephropathies (such as ANA, anti-hepatitis B antigens, rapid plasma reagin . . . ).

The binding partner may be tagged for an easier detection. It may or may not be immobilized on a substrate surface (e.g., beads, array, and the like). For example, an inventive kit may include an array for diagnosing membranous nephropathy as provided herein. Alternatively, a substrate surface (e.g. membrane) may be included in an inventive kit for immobilization of the binding partner (e.g., via electrophoresis and transfer to membrane).

In addition, a kit of the invention generally also comprises at least one reagent for detection of a complex between a binding partner included in the kit and biomarker of the invention.

Depending on the procedure, the kit may further comprise one or more of: extraction buffer and/or reagents, western blotting buffer and/or reagents, and detection means. Protocols for using these buffers and reagents for performing different steps of the procedure may be included in the kit.

The different reagents included in a kit of the invention may be supplied in a solid (e.g. lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale. In certain embodiments, a kit comprises instructions for using its components for the diagnosis, prognosis or monitoring of membranous nephropathy in a patient according to a method of the invention. Instructions for using the kit according to methods of the invention may comprise instructions for processing the biological sample obtained from the subject and/or for performing the test, or instructions for interpreting the results. A kit may also contain a notice in the form in prescribed by a governmental agency regulating the manufacture, use or sale of pharmaceuticals or biological products.

Diagnostic Method Based on Defection of THSD7A mRNA Level

In another embodiment, the invention relates to an in vitro method for diagnosing and/or prognosing membranous nephropathy, particularly idiopathic membranous nephropathy in a patient, comprising the step of determining the level of THSD7A expression in a biological sample obtained from said patient.

In a particular embodiment, said method comprises the following steps:
(i) Measuring the level of THSD7A mRNA in a biological sample obtained from said patient,
(ii) Comparing said level to a reference level,
wherein an increased level of THSD7A mRNA compared to said reference level is indicative of a membranous nephropathy, particularly an idiopathic membranous nephropathy.

Preferably, the biological sample is a blood sample or a kidney biopsy.

Typically, an increased level of THSD7A mRNA corresponds to an increase of at least 20%, preferably at least 50% of the mRNA level measured in a control sample.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). In a preferred embodiment, the mRNA level of THSD7A is determined by RT-PCR, preferably quantitative or semi-quantitative RT-PCR, even more preferably real-time quantitative or semi-quantitative RT-PCR.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single--stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6× SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

Therapeutic Methods of the Invention

The inventors highlighted that the THSD7A protein, which is expressed on podocytes, is an autoantigen in certain cases of membranous nephropathy, which permits to envisage novel therapeutic approaches based on targeting this autoantigen.

Indeed, as described in the prior art, in particular for PLA2R1, the immune deposits resulting from autoantibodies binding to target antigens on podocyte foot can activate the complement system leading to podocyte injury.

Thus, a further object of the invention relates to a method for treating membranous nephropathy, particularly idiopathic membranous nephropathy, in a patient, the method comprising removing anti-THSD7A autoantibodies from a sample in said patient ex vivo.

In one embodiment, the membranous nephropathy is an idiopathic membranous nephropathy.

In another embodiment, the patient is a THSD7A-positive patient.

Preferably, the patient is a human patient.

The antibody can be removed from the blood by immunoabsorption with a THSD7A polypeptide or a fragment thereof as an antigen. The sample is returned back into the patient after the removal of antibodies.

The immunoabsorption of autoantibodies against THSD7A helps to reduce the amount of circulating autoantibodies, particularly circulating THSD7A autoantibodies and thereby reducing the potential damage to the kidney. This treatment can be applied initially after immunological confirmation of the presence of anti-THSD7A autoantibodies and before the start of any immunosuppressive therapy. This is especially useful during this early period before the immunosuppressive therapy can have an effect on the immune system and production of autoantibody in the patient. This treatment may also be applied at any time during the treatment and after diagnosis of said patient as a positive-THSD7A patient.

In one embodiment, immunoabsorption of anti-THSD7A autoantibodies can occur by passing the blood, serum or plasma over an immobilized THSD7A polypeptide. Recombinant THSD7A, preferably recombinant human THSD7A, or fragments can be immobilized on inert and sterile matrices that are known in the art, such as Sepharose beads. The anti-THSD7A autoantibodies will bind to the immobilized THSD7A polypeptide or fragments and remind bound to the matrix indirectly. The blood, serum or plasma is then collected. This resultant blood, serum or plasma should have reduced or no detectable anti-THSD7A autoantibodies. The immunoabsorption procedure should be conducted under sterile conditions. The collect blood, serum or plasma that is depleted of anti-THSD7A autoantibodies can then be transfused back into the patient.

As used in the therapeutic methods of the invention, a fragment of THSD7A polypeptide is typically an antibody-binding fragment.

Another further object of the invention relates to a method for treating a membranous nephropathy, particularly idiopathic membranous nephropathy, in a patient, the method comprising administering a therapeutically effective amount of a THSD7A polypeptide or a fragment thereof, a vector expressing said THSD7A polypeptide or a fragment thereof or a host cell expressing said THSD7A polypeptide or a fragment thereof.

In one embodiment, the membranous nephropathy is an idiopathic membranous nephropathy.

In another embodiment, the patient is a THSD7A-positive patient.

Preferably, the patient is a human patient.

According to the invention, the THSD7A polypeptide or fragments thereof is administered in a soluble form.

By providing soluble THSD7A polypeptide or fragments thereof, the soluble polypeptide can function as decoy antigens and sequester the autoantibodies away from the THSD7A in the renal glomeruli, thereby reducing the potential damage to the kidney. The THSD7A polypeptide is preferably a THSD7A polypeptide of human origin.

In one embodiment, the fragments suitable for treatment or adsorption of the autoantibodies to THSD7A from the serum are fragments comprising or consisting of the extracellular domain of THSD7A or a fragment thereof constituted by one or several of its distinct thrombospondin type I domains and/or linker stalks.

As described above, THSD7A polypeptides and fragments may be synthetized by any method well known in the art, such as, for example, recombinant protein synthesis in bacteria, mammal, insect, yeast or plant cells.

Conventional polymerase chain reaction (PCR) cloning techniques can be used to clone a nucleic acid encoding a THSD7A, using the mRNA of the THSD7A as the template for PCR Cloning. As described above, an exemplary human native THSD7A mRNA sequence is provided in NM_015204 (GeneBank).

Ideally, restriction enzyme digestion recognition sites should be designed at the ends of the sense and anti-sense strand of the PCR primers to facilitate ligation of the amplified nucleic acid into a cloning vector or other vectors. Alternatively, a 3'-A overhang can be included for the purpose of TA-cloning that is well known in the art. Such coding nucleic acids with 3'A overhangs can be easily ligated into the Invitrogen topoisomerase-assisted TA vectors such as pCR -TOPO, pCR®-Blunt II-TOPO, pENTR/D-TOPO®, and pENTR/SD/D-TOPO®. The coding nucleic acid can be cloned into a general purpose cloning vector such as pUC19, pBR322, pBLUESCRIPT vectors (STRATAGENE Inc.) or pCR TOPO® from INVITROGEN INC. The resultant recombinant vector carrying the nucleic acid encoding a THSD7A can then subcloned into protein expression vectors or viral vectors for the synthesis of THSD7A fusion protein in a variety of protein expression systems using host cells selected front the group consisting of mammalian cell lines, insect cell lines, yeast, bacteria, and plant cells. Protease cleavage sites can also be designed and included within the nucleic acid to facilitate the liberation of THSD7A from a larger fusion protein, e.g. His-THSD7A or thioredoxin-THSD7A. Examples of protease cleavage sites include but are not limited to those of enterokinase, chymotrypsin, and thrombin.

PCR amplified coding nucleic acids can be cloned into a vector using the TOPO® cloning method in INVITROGEN topoisomerase-assisted TA vectors such as pCR®-TOPO, pCR®- Blunt II-TOPO®, pENTR/D-TOPO®, and pENTR/SD/D-TOPO®. Both pENTR/D-TOPO®, and pENTR/SD/D-TOPO® are directional TOPO entry vectors which allow the cloning of the DNA sequence in the 5'->3' orientation into a GATEWAY® expression vector. Directional cloning in the 5'->3' orientation facilitate the unidirectional insertion of the DNA sequence into a protein expression vector such that the promoter is upstream of the 5' ATG start codon of the nucleic acid, thus enabling promoter-driven protein expression. The recombinant vector carrying a THSD7A coding nucleic acid can be transfected into and propagated in a general cloning *E. coli* cells such as XLIBlue, SURE (STRATAGENE) and TOP-10 cells (INVITROGEN).

Different expression vectors are available for the expression and purification of a recombinant protein produced from a heterologous protein expression system can be made. Heterologous protein expression systems that use host cells selected from, e.g., mammalian, insect, yeast, bacterial, or plant cells are well known to one skilled in the art. The expression vector should have the necessary 5' upstream and 3' downstream regulatory elements such as promoter sequences, ribosome recognition and binding TATA box, and 3' UTR AAUAAA transcription termination sequence for efficient gene transcription and translation in its respective host cell. The expression vector may have additional sequence such as 6×-histidine, V5, thioredoxin, glutathione-S-transferase, c-Myc, VSV-G, HSV, FLAG, maltose binding peptide, metal-binding peptide, HA and "secretion" signals (Honeybee melittin, [alpha]-factor, PHO, Bip), which are incorporated into the expressed recombinant protein. In addition, there can be enzyme digestion sites incorporated after these sequences to facilitate enzymatic removal of additional sequence after they are not needed. These additional sequences are useful for the detection of recombinant protein expression, for protein purification by affinity chromatography, enhanced solubility of the recombinant protein in the host cytoplasm, for better protein expression especially for small protein fragments and/or for secreting the expressed recombinant protein out into the culture media, into the periplasm of the prokaryote bacteria, or to the spheroplast of yeast cells. The expression of recombinant protein can be constitutive in the host cells or it can be induced, e.g., with copper sulfate, sugars such as galactose, methanol, methylamine, thiamine, tetracycline, infection with baculo virus, and (isopropyl-beta-D-thiogalactopyranoside) IPTG, a stable synthetic analog of lactose.

In some embodiments, recombinant THSD7A can be expressed in a variety of expression host cells e. g., bacteria, such as E. coli, yeast, mammalian, insect, and plant cells such as Chlamydomonas, or even from cell-free expression systems. From a cloning vector, the nucleic acid can be subcloned into a recombinant expression vector that is appropriate for the expression of the protein in mammalian, insect, yeast, bacterial, or plant cells or a cell-free expression system such as a rabbit reticulocyte expression system. Subcloning can be achieved by PCR cloning, restriction digestion followed by ligation, or recombination reaction such as those of the lambda phage-based site-specific recombination using the Gateway® LR and BP CLONASE™ enzyme mixtures. Subcloning should be unidirectional such that the 5' ATG start codon of the nucleic acid is downstream of the promoter in the expression vector. Alternatively, when the coding nucleic acid is cloned into pENTR/D-TOPO®, pENTR/SD/D-TOPO® (directional entry vectors), or any of the Invitrogen's GATEWAY® Technology pENTR (entry) vectors, the coding nucleic acid can be transferred into the various GATEWAY® expression vectors (destination) for protein expression in mammalian cells, E. coil, insects and yeast respectively in one single recombination reaction. Some of the GATEWAY® destination vectors are designed for the constructions of baculovirus, adenovirus, adeno-associated virus (AAV), retrovirus, and lentiviruses, which upon infecting their respective host cell, permit heterologous expression of the recombinant protein in the host cells. Transferring a gene into a destination vector is accomplished in just two steps according to manufacturer's instructions. There are GATEWAY® expression vectors for protein expression in E. coli, insect cells, mammalian cells, and yeast. Following transformation and selection in E. coli, the expression vector is ready to be used for expression in the appropriate host.

Examples of other expression vectors and host cells are the pET vectors (NOVAGEN), pGEX vectors (Amersham Pharmacia), and pMAL vectors (New England labs, Inc.) for protein expression in E. coli host cells such as BL21, BL21(DE3) and AD494(DE3)pLysS, Rosetta (DE3), and Origami(DE3) (NOVAGEN); the strong CMV promoter-based pcDNA3.1 (INVITROGEN) and pCIneo vectors (Promega) for expression in mammalian cell lines such as CHO, COS, HEK-293, Jurkat, and MCF-7; replication incompetent adenoviral vector vectors pADENO X, pAd5F35, pLP-ADENO-X-CMV (CLONTECH), pAd/CMV/V5-DEST, pAd-DEST vector (INVITROGEN) for adenovirus-mediated gene transfer and expression in mammalian cells; pLNCX2, pLXSN, and pLAPSN retrovirus vectors for use with the RETRO-C™ system from Clontech for retroviral-mediated gene transfer and expression in mammalian cells; pLenti4/V5-DEST™, pLenti6/V5-DEST™, and pLenti6.2/V5-GW/lacZ (INVITROGEN) for lentivirus-mediated gene transfer and expression in mammalian cells; adenovirus-associated virus expression vectors such as pAAV-MCS, pAAV-IRES-hrGFP, and pAAV-RC vector (STRATAGENE) for adeno-associated virus-mediated gene transfer and expression in mammalian cells; BACpak6 baculo virus (CLONTECH) and pFASTBAC™ (INVITROGEN) for the expression in Spodopera frugiperda 9 (Sf9) and Sal insect cell lines; pMT/BiP/V5-His (INVITROGEN) for the expression in Drosophila Schneider S2 cells; Pichia expression vectors pPICZα, pPICZ, pFLDα and pFLD (INVITROGEN) for expression in Pichia pastoris and vectors pMETα and pMET for expression in P. methanolica; pYES2/GS and pYD1 (INVITROGEN) vectors for expression in yeast Saccharomyces cerevisiae. Recent advances in the large scale expression heterologous proteins in Chlamydomonas reinhardtii are described by Griesbeck C. et. al. 2006 MoI. Biotechnol. 34:213-33 and Fuhrmann M. 2004, Methods Mol Med. 94:191-5. Foreign heterologous coding sequences are inserted into the genome of the nucleus, chloroplast and mitochondria by homologous recombination. The chloroplast expression vector p64 carrying the versatile chloroplast selectable marker aminoglycoside adenyl transferase (aadA), which confers resistance to spectinomycin or streptomycin, can be used to express foreign protein in the chloroplast. The holistic gene gun method can be used to introduce the vector in the algae. Upon its entry into chloroplasts, the foreign DNA is released from the gene gun particles and integrates into the chloroplast genome through homologous recombination.

Recombinant protein expression in the different host cells can be constitutive or inducible with inducers such as copper sulfate, sugars such as galactose, methanol, methylamine, thiamine, tetracycline, or IPTG. After the protein is expressed in the host cells, the host cells are lysed to liberate the expressed protein for purification, Methods of lysing the various host cells are featured in "Sample Preparation-Tools for Protein Research" EMD Bioscience and in the Current Protocols in Protein Sciences (CPPS). A preferred purification method is affinity chromatography such as ion-metal affinity chromatograph using nickel, cobalt, or zinc affinity resins for histidine-tagged recombinant protein. Methods of purifying histidine-tagged recombinant proteins are described by CLONTECH using their TALON® cobalt resin and by NOVAGEN in their pET system manual, 10th edition. Another preferred purification strategy is by immuno-affinity chromatography, for example, anti-myc antibody conjugated resin can be used to the affinity purify rnyc-tagged recombinant peptide. Enzymatic digestion with serine proteases such as thrombin and enterokinase cleave and release the recombinant protein from the histidine or myc tag, releasing the recombinant protein from the affinity resin while the histidine-tags and myc-tags are left attached to the affinity resin.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. As an example, large scale cell-free production of the integral membrane protein EmrE multidrug transporter is described by Chang G. el. al., Science 310:1950-3 (2005).

Other commercially available cell-free expression systems include the EXPRESSWAY™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E. coli*-based in-vitro system; and the TNT Coupled Reticulocyte Lysate Systems (Promega) which uses a rabbit reticulocyte-based in-vitro system.

In one embodiment, a cocktail of several THSD7A polypeptides is used for treatment. Envisioned peptides can be fused with other proteins for longer serum half-life, tandemly linked peptides or circular peptides.

Encompassed in the methods described herein is a mammalian THSD7A that is purified from a mammal, e. g. a pig or a rabbit. In one embodiment, the native (non-recombinant) mammalian THSD7A is purified from the kidneys ex vivo. Methods of native protein purification are well known to the one skilled in the art.

A still further object of the invention relates to a THSD7A polypeptide or a fragment thereof for use in the treatment of membranous nephropathy, particularly idiopathic membranous nephropathy.

In one embodiment, the membranous nephropathy is an idiopathic membranous nephropathy.

In another embodiment, the patient is a THSD7A-positive patient.

Preferably, the patient is a human patient.

In a preferred embodiment, said fragment of THSD7A polypeptide is an antibody-binding fragment (which means according to the invention that autoantibodies of patient afflicted with an idiopathic membranous nephropathy recognize said fragment).

Preferably, said fragment of THSD7A comprises or consists of the extracellular domain of THSD7A or a fragment thereof constituted by one or several of its distinct thrombospondin type I domains and/or linker stalks.

According to the invention, said THSD7A polypeptide or a fragment thereof is used in a therapeutically effective amount.

In a particular embodiment, the invention also provides a vector expressing said THSD7A polypeptide or a fragment thereof or a host cell expressing said THSD7A polypeptide or a fragment thereof.

A further object of the invention relates to a pharmaceutical composition comprising a THSD7A polypeptide or a fragment thereof and a pharmaceutically acceptable carrier. In a further aspect, the invention pertains to said pharmaceutical composition for use for treating membranous nephropathy.

In one embodiment, the membranous nephropathy is an idiopathic membranous nephropathy.

In another embodiment, the patient is a THSD7A-positive patient

Preferably, the patient is a human patient.

In a particular embodiment, said pharmaceutical composition may comprise a vector expressing said THSD7A polypeptide or a fragment thereof or a host cell expressing said THSD7A polypeptide or a fragment thereof.

The pharmaceutical composition can be a combination of full-length THSD7A and fragments of various sizes, particularly antibody-binding fragments, and a pharmaceutically acceptable vehicle. Examples of such fragments encompass, but are not limited to, fragments comprising or consisting of the extracellular domain of THSD7A or a fragment thereof constituted by one or several of its distinct thrombospondin type I domains and/or linker stalks.

In one embodiment, the pharmaceutical composition of the invention may comprise a cocktail of several THSD7A polypeptides or fragments thereof. Envisioned peptides can be fused with other proteins for longer serum half-life, tandemly linked peptides or circular peptides.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). In one embodiment, other ingredients can be added to pharmaceutical formulations, including antioxidants, e.g., ascorbic acid; low molecular weight (less than about ten residues) polypeptides, polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compositions of the invention can be formulated as neutral or salt forms,

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, to name a few.

Various delivery systems are known in the art and can be used to administer a THSD7A polypeptide or fragments thereof, e.g., encapsulation in liposomes, microparticles, and microcapsules (see, e.g., Wu and Vu, J. Biol. Chem. 262: 4429-4432 (1987)). The composition can be delivered in a vesicle, in particular a liposome (see, Langer, Science, 249:1527-1533 (1990); Treat et al., in Liposomes in the Therapy of Infectious Disease and Cancer, Lopez-Berestein and Fidler, eds. (Liss, N.Y. 1989), pp. 353-365; Lopez-Berestein, ibid., pp. 317-327; see, generally, ibid.). Methods of introduction include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compositions of the invention into the central nervous system by any suitable route, including intraventricular and intrathecal injection; intraventricular injection can be facilitated by an intraventricular catheter, for example, attached to a reservoir, such as an Omcana reservoir. Pulmonary administration can also be employed, e.g., by use of an inhaler or nebulizer, and formulation with an aerosolizing agent.

In one embodiment, the pharmaceutical formulation to be used for therapeutic administration must be sterile. Sterility is readily accomplished by filtration through sterile filtration membranes (e.g., 0.2 micron membranes). The pH of the pharmaceutical formulation typically should be about from 6 to 8.

In one embodiment, the composition can be delivered in a controlled release system. In one embodiment, a pump can be used (see Langer, supra; Sefton, CRC Grit. Ref. Biomed. Eng., 14:201 (1987); Buchwald et al., Surgery, 88:507 (1980); Saudek et al., N. Engl. J. Med., 321:574 (1989)). In another embodiment, polymeric materials can be used (see, Medical Applications of Controlled Release, Langer and Wise, eds. (CRC Press, Boca Raton, Fla. 1974); Controlled Drug Bioavailability, Drug Product Design and Performance, Smolen and Ball, eds. (Wiley, N.Y. 1984); Ranger and Peppas, Macromol. Sci. Rev. Macromol. Chem., 23:61 (1983); see also Levy et al., Science, 228:190 (1985); During et al., Ann. Neurol., 25:35 1 (1989); Howard et al., J. Neurosurg., 71:105 (1989)). Other controlled release systems are discussed in the review by Langer (Science, 249:15274533 (1990)). For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

The precise dose to be employed in the formulation will also depend on the route of administration, and the severity of membranous nephropathy and the titer of anti-THSD7A autoantibodies in the serum, and should be decided according to the judgment of the practitioner and each patient's circumstances. Effective doses can be extrapolated from dose-response curves derived from in vitro or animal model test systems.

The dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. For gene therapy, viral vector should be in the range of $1\times10^6$ to $10^{14}$ viral vector particles per application per patient.

In addition, in vitro or in vivo assays can optionally be employed to help identify optimal dosage ranges. The precise dose to be employed will also depend on the route of administration, and the seriousness of the condition being treated and should be decided according to the judgment of the practitioner and each subject's circumstances in view of, e.g., published clinical studies. Suitable effective dosage amounts, however, range from about 10 micrograms to about 5 grams about every 4 hour, although they are typically about 500 mg or less per every 4 hours. In one embodiment the effective dosage is about 10 µg, about 20 µg, about 50 µg, about 100 µg, about 200 µg, about 300 µg, about 400 µg, about 500 µg, about 600 µg, about 700 µg, about 800 µg, about 900 µg, about 1 mg, about 1.2 mg, about 1.4 mg, about 1.6 mg, about 1.8 mg, about 2.0 mg, about 2.2 mg, about 2.4 mg, about 2.6 mg, about 2.8 mg, about 3.0 mg, about 3.2 mg, about 3.4 mg, about 3.6 mg, about 3.8 mg, about 4.0 mg, about 4.2 mg, about 4.4 mg, about 4,6 mg, about 4.8 mg, or about 5.0 mg, 10.0 mg, 15.0 mg, 20.0 mg, 25.0 mg, 50.0 mg every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered. The compositions comprising THSD7A polypeptide, fragments thereof, or expression vectors and/or host cells comprising it are suitably administered to the patient at one time or over a series of treatments.

In an embodiment, the composition comprising a THSD7A polypeptide or fragments thereof is administered in combination with immunosuppressive therapies including, but not limited to, azathioprine, infliximab, omalizumab, daclizumab, adalimumab, eculizumab, efalizumab, natalizumab omalizumab, cyclophosphamide, chlorambucil, and/or rituximab.

Particularly, the composition comprising a THSD7A polypeptide or fragments thereof is administered in combination with any treatment useful for treating membranous nephropathy, particularly idiopathic membranous nephropathy, and that could be effective for the patient.

The invention will be further illustrated by the following examples. However, these examples should not be interpreted in any way as limiting the scope of the present invention.

EXAMPLES

Material and Methods

Patients. The diagnosis of membranous nephropathy (MN) was made by renal biopsy. Sera were taken from patients with membranous nephropathy, patients with other kidney diseases, and healthy controls. All patients were without previous immunosuppressive therapy at the time the first serum was taken. Sera were investigated for anti-PLA2R1 antibodies by means of ELISA.

Human renal tissue. Healthy parts of kidneys from patients who underwent nephrectomy were used for the preparation of an extract of human glomeruli. Glomeruli were gained by graded sieving and dounce-homogenized. Soluble and membrane fractions were separated by ultracentrifugation and solubilization. To remove present immunoglobulin G, samples were incubated with Protein G microbeads (Miltenyi Biotech, Bergisch Gladbach, Germany) and bound immunoglobulins were extracted by magnetic separation columns (idem). For enzymatic deglycosylation the inventors used N-glycopeptidase F and Neuraminidase according to the manufacturer's instructions (both Roche Diagnostics, Mannheim, Germany).

Western blot analysis. Protein samples were electrophoresed in polyacrylamide gels under non-reducing or reducing conditions and transferred to PVDF membranes under semi-dry conditions (BioRad, Hercules, USA). Membranes (Millipore, Billerica, USA) were blocked with 5% dry milk in PBS-Tween 0.05% overnight and subsequently incubated with primary and secondary antibodies for 2 hours at room temperature. For use as the primary antibody, sera were diluted at a 1:100 working dilution in 0.5% dry milk. For specific detection of THSD7A (Thrombospondin type domain containing 7A) the inventors used a commercially available rabbit polyclonal antibody (Sigma, St. Louis, USA) at a working dilution of 1:1,000. Secondary antibodies were horseradish peroxidase-conjugated mouse anti-human or goat anti-rabbit IgG (all SouthernBiotech, Birmingham, USA). When IgG subclass detection was desired, mouse anti-human IgG1-IgG4 were applied (idem).

Immunoprecipitation Human glomerular lysates were incubated with sera from patients with membranous nephropathy or other glomerular diseases, and from healthy controls. IgG4 affinity matrix (Life Technologies, Leiden, Netherlands) was added and samples were incubated overnight at 4° C. Immunoprecipitates were collected by low-speed centrifugation and samples were electrophoresed, blotted, and detected with anti-THSD7A antibody as described above.

Mass spectrometry. Gel regions corresponding to visible bands in Western blot analysis were excised and subjected to tryptic in-gel digestion. Digested peptides were isolated using formic acid and acetonitrile, separated by means of nano high performance liquid chromatography (nanoHPLC), and identified by matrix-assisted laser desorption/ionization-time of flight (MALDI-TOF) tandem mass spectrometry using an ABI 4700 mass spectrometer (AB Sciex, Framingham, USA). Raw data were analyzed by ProteinPilot software (AB Sciex, Framingham, USA) and further processed using the Paragon Algorithm.

Recombinant expression of candidate proteins. Human cDNAs coding for THSD7A and the three paralogs of PLA2R1, i.e. the macrophage mannose receptor (MRC1), the endocytic receptor 180 (MRC2), and the dendritic cell receptor 205 (LY75), were cloned by PCR using standard methods or purchased from companies (Gene Coppoeia and OriGene). All cDNA sequences were verified by sequencing after subcloning into mammalian expression vectors and addition of specific HA or DDK tags (pLPCX or pCMV6 entry). Plasmids were transiently transfected into HEK293 cells by calcium phosphate transfection. After 72 hours, the medium was collected and cells were scraped and lyzed. The soluble fraction of the expressed protein of interest was obtained by ultracentrifugation. The membrane fraction was resuspended in lysis buffer, homogenized by vigorous manual douncing, and the solubilized fraction was obtained after high speed centrifugation. Expression of the candidate proteins was verified by Western blot analysis using specific antibodies and compared to mock transfection.

Histological analysis. For immunofluorescence analyses, 2 µM paraffin sections of the healthy pole of a human tumor nephrectomy specimen were deparaffinized and rehydrated in water. Antigen retrieval was obtained by boiling in citrate buffer pH 6.1 (30 min at constant 98° C.). Nonspecific binding was blocked with 5% horse serum (Vector. Burlingame, USA) with 0.05% Triton X-100 (SIGMA, St. Louis, USA) in PBS for 30 min at RT prior to incubation at 4° C. o/n with primary antibodies in blocking buffer. .Staining was visualized with fluorochrome-conjugated secondary antibodies (Jackson Immunoresearch, Dianova, Hamburg, Germany; 1:400, 30 min RT in 5% horse serum). Nuclei were visualized using DRAQ5 (Molecular Probes, LIFE TECHNOLOGIES, Grand Island, USA). Negative controls were performed omitting primary antibodies. Stained sections were evaluated by confocal microscopy using the Laser Scanning Microscope 510 and appropriate software (ALL ZEISS, OBERKOCHEN, Germany).

For immunohistochemistry, 1 µM paraffin sections of renal biopsies from patients with MN were deparaffinized and rehydrated. Antigen retrieval was obtained by boiling in DAKO antigen retrieval buffer, pH 9 (15 min at 98° C.) and subsequent cooling at RT for 15 min. Nonspecific binding was blocked with 5% horse serum (Vector) with 0.05% Triton X-100 (SIGMA) in PBS for 30 mm at RT prior to incubation at 4° C. o/n with rabbit anti-THSD7A (1:400, Atlas) in blocking buffer. Staining was visualized with the ZytochemPlus AP Polymer kit (ZYTOMED SYSTEMS) according to the manufacturer's instruction. Nuclei were counterstained with hemalaun and sections were mounted with gum Arabic (SIGMA). Negative controls were performed omitting primary antibodies. Stainings were evaluated with an Axioskop using the Axiovision software (ALL ZEISS).

Primary antibodies used for histological analyses were: rabbit anti-THSD7A and anti-PLA2R1 (ATLAS, 1:200), guinea-pig anti-nephrin (ACRIS, 1:100), goat anti-collagen Type IV (SOUTHERNBIOTECH, 1:400), and sheep anti-fibronectin (DAKO, 1:500). All secondary antibodies were fluorochrome-conjugated affinity purified donkey antibodies (JACKSON IMMUNORESEARCH, Dianova, Hamburg, Germany, 1:400).

Results

Screening of idiopathic membranous nephropathy sera with the paralogs of PLA2R1 and a protein lysate from human glomeruli. We screened idiopathic membranous nephropathy (iMN) sera and relevant control sera by two parallel approaches. The first one was focused on the paralogs of PLA2R1 as candidate antigens. The second one was more general, screening the sera on total proteins from a human glomerular extract (HGE).

The three paralog proteins of PLA2R1, i.e. the macrophage mannose receptor (MRC1), the endocytic receptor 180 (MRC2), and the dendritic cell receptor 205 (LY75) were transiently expressed as recombinant proteins in HEK293 cells. Serum reactivity against these paralogy as well as HGE was investigated by Western blot analysis under non-reducing conditions with sera from 65 patients with membranous nephropathy (of which 30 were negative for anti-PLA2R1 antibodies), 57 patients with other proteinuric kidney diseases and 44 healthy controls. All sera that were known to be positive for anti-PLA2R1 antibodies, as tested previously by ELISA, reacted with recombinant PLA2R1 on Western blot analysis, but none of these sera nor sera from other categories reacted with the paralog proteins of PLA2R1. Sera from 4 patients with iMN, who were all negative for anti-PLA2R1 antibodies, recognized the same glomerular protein of about 250 kDa in size (FIG. 1A). Sera from patients with other kidney diseases or from healthy controls did not show any reactivity in this area. The screening was then extended to 129 patients with membranous nephropathy (95 with iMN and 34 with secondary MN). A total of 6 sera, all negative for anti-PLA2R1 antibodies in ELISA and Western blot analysis, were found to react with the same protein of 250 kDa (FIG. 1B). Among these patients, 5 had iMN and 1 had MN with a positive titer for anti-nuclear antibodies (ANA), classifying this patient as a case of secondary MN (FIG. 1B).

The above screening thus identified a novel autoantigen of 250 kDa present in HGE, likely distinct from PLA2R1 which has a size of about 180 kDa in the same HGE preparation. To better discriminate between the two antigens, we ran the HOE proteins on SDS-PAGE gels with low acrylamide percentage to separate the two proteins of interest, then prepared Western blots and sequentially incubated the membranes with sera reactive against PLA2R1 or the new antigen. As expected, two distinct bands with a size difference of about 60 kDa were revealed, indicating the presence of two different antigens. To further characterize the novel antigen in comparison with PLA2R1, we enzymatically deglycosylated HGE containing the two antigens. N-glycopeptidase F decreased the size of the novel antigen to approximatively 225 kDa. and the addition of Neuraminidase, an enzyme that removes sialic acid, caused a further shift to 200 kDa. On the other hand, PLA2R1 migrated to approximatively 145 kDa after the addition of N-glycopeptidase F, as described previously3, but no more shift was seen after addition of Neuraminidase. All sera reacting with the fully glycosylated 250 kDa protein also recognized the deglycosylated forms at the same molecular mass, suggesting that all sera recognize the same protein. Moreover, both the novel antigen and PLA2R1 are present in the membrane fraction of HGE, but only PLA2R1 is present in the soluble fraction.

Identification of the novel HGE antigen as THSD7A. We performed gel electrophoresis of native glomerular proteins and glomerular proteins treated with N-glycopeptidase F as well as N-glycopeptidase F and Neuraminidase. The greater part of the proteins from each treatment was stained with Coomassie blue dye and the other part was transferred to PVDF and probed with a patient's serum positive for antibodies against the novel antigen. We then excised the Coomassie-stained gel areas corresponding to the Western blot signals at 250 kDa, 225 kDa and 200 kDa as described above, assuming that the target protein would be specifically present in all three conditions. Mass spectrometric analysis was performed in all gel slices and a primary candidate list was obtained. The candidate proteins were ranked according to the expected biochemical characteristics of the new antigen, i.e. by reference to their molecular mass, N-glycosylation, membranous localization, and expression in human kidney or glomeruli. Interestingly, all the previously tested paralogs of PLA2R1 appeared in the mass spectrometric analysis in a prominent position, retrospectively justifying the initial approach. We used commercially available antibodies and transiently transfected HEK293 cells to specifically test for candidate antigens and eventually identified thrombospondin type I domain containing 7A (THSD7A) as the protein of interest.

Figure 2:
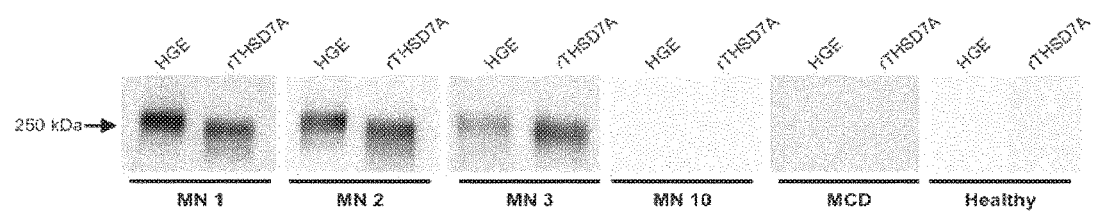
FIG. 2: Identification of the target antigen. A. Results of western blotting of a human glomerular extract (HGE) and transfected HEK(293 cells overexpressing thrombospondin type 1 domain containing 7A (rTHSD7A) with reactive and non-reactive sera. This panel shows representative images of three patients with membranous nephropathy (MN) whose sera reacted with both, HGE and rTHSD7A (MN 1 to MN 3), one non-reactive MN patient (MN 36), one non-reactive patient with minimal change disease (MCD), and one non-reactive healthy control patient. rTHSD7A migrated to a slightly lower position than the native protein contained in the glomerular lysate, most likely due to a difference in post-translational modification. B. Results of immunoprecipitation of THSD7A from a lysate of a human glomerular extract (HGE). HGE were incubated with reactive and non-reactive serum samples from patients with MN and controls, followed by the addition of human IgG4 affinity matrix. Samples were centrifuged and immunoprecipitates were electrophoresed under reducing conditions, blotted on PVDF membranes and detected with a polyclonal rabbit anti-THSD7A antibody. All five reactive sera from patients with MN immunoprecipitated the target antigen from HGE (MN 1 to MN 5), whereas one non-reactive MN serum (MN 9) as well as one serum from a healthy control patient did not. No immunoprecipitation occured when serum was replaced by water in the experiment.
Figure 2:
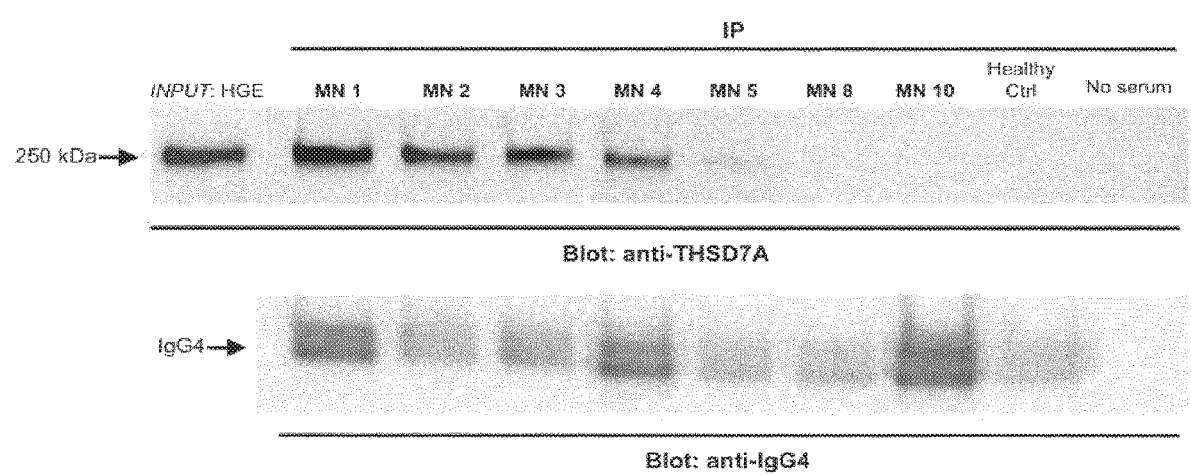

Indeed, all the 6 sera previously reacting with the 250 kDa protein in HGE, but none of the anti-PLA2R1 positive sera or controls, also recognized recombinant THSD7A expressed in HEK293 cells (FIG. 2A). Of note, the native THSD7A protein present in HGE and the recombinant protein expressed in HEK293 cells showed the same pattern of glycosylation, yet the recombinant protein migrated to a slightly lower position, suggesting a minor difference in post-translational modification (FIG. 2A). As a final proof that the glomerular autoantigen recognized by the reactive sera was indeed THSD7A, we performed immunoprecipitation experiments. All reactive sera, but not controls, immunoprecipitated THSD7A from HGE, as demonstrated by the reactivity of precipitates with a specific polyclonal antibody against THSD7A (FIG. 2B).

Characterization of anti-THSD7A autoantibodies. To determine the IgG subtype(s) of anti-THSD7A autoantibodies, we used secondary antibodies against the different IgGs (1 to 4). Anti-THSD7A IgG4 was found to be the predominant antibody for all 6 reactive sera. However, other IgG subtypes were also present in most sera. This finding was in accordance with enhanced staining for IgG4 in all available biopsies. Moreover, all of the positive sera lost their reactivity to both the 250 kDa protein in HGE, and recombinant THSD7A when gels were run under reducing conditions. Thus, as for anti-PLA2R1 autoantibodies, the anti-THSD7A autoantibodies are mostly IgG4 and recognize one or more conformation-dependent epitope(s) in THSD7A which are present in both native and recombinant THSD7A proteins.

Figure 3:
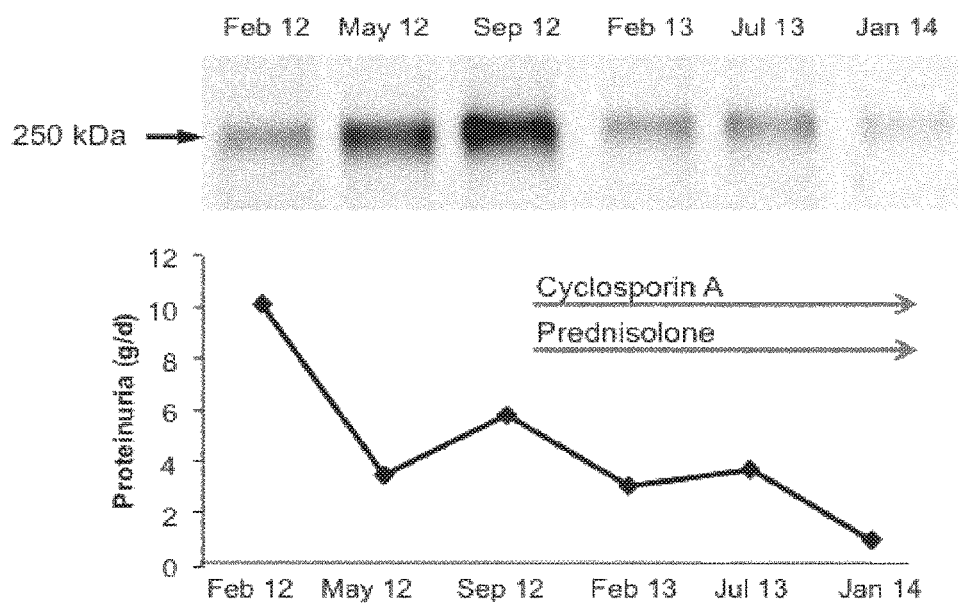
FIG. 3: Relationship between anti-THSD7A antibodies and the clinical course of MN patients. Results of western blotting of equal volumes of human glomerular extract (HGE) with serial serum samples from one patient with membranous nephropathy. After an initial decrease in proteinuria, the patient developed severe edema and heavy proteinuria in September 2012. Immunosuppressive treatment with cyclosporine A and steroids was initiated and the proteinuria decreased until the patient reached partial remission in January 2014. This development of disease activity is reflected by a decrease of the western blot signal after initiation of immunosuppressive treatment.

Anti-THSD7A autoantibodies and disease activity. Serial serum samples from two patients with iMN and positive for anti-THSD7A antibodies were available for analysis of anti-THSD7A antibody levels by semi-quantitative Western blot analysis. In one patient, immunosuppressive therapy induced a substantial decrease of the anti-THSD7A antibody level, which was followed by a reduction in proteinuria (FIG. 3). On the other hand, in one patient who did not receive immunosuppressive therapy due to minor clinical complaints, the antibody level remained steadily high, with a sustained nephrotic-range proteinuria. Taken together, these results suggest an association between the antibody level and clinical disease activity.

Glomerular expression of THSD7A in healthy controls and MN patients. In order to investigate the glomerular expression of THSD7A, we performed immunofluorescent and immunohistochemical analyses in biopsy samples from healthy subjects and from patients with iMN. We found a prominent linear glomerular expression of THSD7A in biopsy specimens from healthy kidneys when probed with two different anti-THSD7A specific antibodies. The negative controls omitting the primary antibody showed no staining at all. When stained for nephrin, a transmembrane protein that is expressed in the region of the intercellular slit-diaphragm of podocyte foot processes, a very similar staining pattern as for THSD7A was seen. Moreover, both molecules showed strong co-localization, suggesting that THSD7A is located in or at close proximity of podocyte foot processes. On the other hand, THSD7A did not co-localize with markers of the glomerular basement membrane, such as collagen type IV and fibronectin. Precisely, THSD7A was located subepithelially relative to collagen type IV and fibronectin, suggesting that it is expressed on podocyte foot processes rather than the glomerular basement membrane.

It is known from previous studies that PLA2R1 co-localizes with IgG4 in the subepthelial deposits of biopsies from patients with MN and detectable antibodies against PLA2R1. In order to investigate this phenomenon in anti-THSD7A positive MN patients, we performed immunofluorescence microscopy with specific anti-THSD7A as well as anti-IgG4 antibodies. We found strong staining for IgG4 and THSD7A in all available biopsies from patients with anti-THSD7A positive MN (n=5). Thereby, THSD7A co-localized with IgG4 in a granular pattern that is typical for MN.

Immunohistochemical staining of THSD7A revealed a linear positivity along podocyte plasma membranes in the biopsy samples from healthy controls. In contrast, PLANO is slightly less expressed. In all five available biopsies from patients with anti-THSD7A positive MN, immunohistochemistry revealed markedly enhanced staining for THSD7A when compared with normal controls. On the other hand, PLA2R1 staining was normal in these patients. in contrast, all investigated patients with anti-PLA2R1 antibodies had normal staining for THSD7A, but enhanced granular staining of PLA2R1, as described previously. All investigated biopsies from patients with secondary MN had normal staining for both THSD7A and PLA2R1.

Elution of anti-THSD7A IgG from biopsy tissue. IgG was acid eluted from from the frozen remnant biopsy core from one patient whose serum was reactive with THSD7A, from two cases of PLA2R1-associated iMN, and from a case of class V lupus nephritis. IgG from the anti-THSD7A-seropositive case specifically recognized recombinant THSD7A on Western blot, while IgG eluted from the PLA2R1-associated MN cases did not recognize THSD7A and specifically recognized PLA2R1. IgG eluted from the class V lupus nephritis biopsy recognized neither antigen.

The invention claimed is:

1. An in vitro method for diagnosing and/or prognosing membranous nephropathy in a patient, said method comprising:
   detecting in a biological sample obtained from said patient one or more autoantibodies recognizing a Thrombospondin, Type I, Domain Containing 7A (THSD7A) protein; the detection comprising:
   immobilizing THSD7A protein or an antibody-binding fragment thereof on a solid surface, wherein the THSD7A protein or the antibody-binding fragment thereof is used for the detection of the autoantibodies and wherein said THSD7A protein is heterologously expressed in a mammalian cell;
   contacting the biological sample to the THSD7A protein or the antibody-binding fragment thereof;
   incubating a labelled antibody that recognizes antibodies from a species of the biological sample; and
   detecting the labelled antibody.

2. The in vitro method according to claim 1, said method comprising:
   detecting an antigen-antibody complex formed,
   wherein the presence of the antigen-antibody complex is indicative of membranous nephropathy.

3. The in vitro method according to claim 1, wherein said membranous nephropathy is an idiopathic membranous nephropathy.

4. The in vitro method according to claim 1, wherein said biological sample is a blood sample.

5. The in vitro method according to claim 1, wherein said patient is a secretory phospholipase A2 receptor (PLA2R1)-negative patient.

6. An in vitro method for diagnosing and/or prognosing membranous nephropathy in a patient, said method comprising:
   obtaining a kidney biopsy sample from the patient, the patient having membranous nephropathy or being suspected of having membranous nephropathy;
   contacting the biological sample with an antibody or a fragment of an antibody that recognizes THSD7A, wherein the antibody or the fragment of the antibody is labelled with a detectable molecule or substance;
   determining a level of a THSD7A protein in a biological sample obtained from said patient based upon a level of binding of the THSD7A to the antibody or the fragment of the antibody that recognizes THSD7.

7. The in vitro method according to claim 6, said method comprising:
   (i) measuring the level of the THSD7A protein in the kidney biopsy sample obtained from said patient, and
   (ii) comparing said level to a reference level,
   wherein an increased level of the THSD7A protein compared to said reference level is indicative of membranous nephropathy.

8. The in vitro method according to claim 6, wherein said membranous nephropathy is idiopathic membranous nephropathy.

9. A method of detecting whether a patient is suffering from membranous nephropathy, the method comprising:
   obtaining a sample from the patient suspected of being afflicted with membranous nephropathy,
   detecting the presence or absence of an antibody against a THSD7A polypeptide or an antibody-binding fragment thereof in the sample from the patient, and
   detecting a level of the antibody against the THSD7A polypeptide or an antibody-binding fragment thereof in the sample by contacting the sample with the THSD7A polypeptide or an antibody-binding fragment thereof and detecting binding between the antibody and the THSD7A polypeptide or an antibody-binding fragment thereof,
   wherein the presence of an increased level of the antibody against a THSD7A polypeptide or an antibody-binding fragment thereof in the sample, compared to the level of a healthy individual, indicates membranous nephropathy in the patient.

10. A method of detecting an antibody against a THSD7A polypeptide or an antibody-binding fragment thereof in a patient, the method comprising:
    obtaining a sample from a patient having membranous nephropathy or suspected of being afflicted with membranous nephropathy, and
    detecting whether the antibody against a THSD7A polypeptide or an antibody-binding fragment thereof is present in the sample by contacting the sample with the THSD7A polypeptide or an antibody-binding fragment thereof and detecting binding between the antibody and the THSD7A polypeptide or an antibody-binding fragment thereof.

11. A method of diagnosing and treating membranous nephropathy in a patient, the method comprising:
    obtaining a sample from a patient suspected to be afflicted with membranous nephropathy, detecting whether an antibody against a THSD7A polypeptide or an antibody-binding fragment thereof is present in the sample, diagnosing the patient with membranous nephropathy when the presence of the antibody against a THSD7A polypeptide or an antibody-binding fragment thereof is detected, and performing immunoabsorption of the antibody against the THSD7A polypeptide or the antibody-binding fragment thereof by passing blood, serum, or plasma of the patient over an immobilized THS7DA polypeptide or fragment thereof.

* * * * *

UNITED STATES PATENT AND TRADEMARK OFFICE
CERTIFICATE OF CORRECTION

PATENT NO. : 10,670,597 B2
APPLICATION NO. : 16/106141
DATED : June 2, 2020
INVENTOR(S) : Lambeau et al.

It is certified that error appears in the above-identified patent and that said Letters Patent is hereby corrected as shown below:

On the Title Page

Item (57) The Abstract currently reads:
"An in vitro method can diagnose membranous nephropathy patient. The method includes detecting in a biological sample obtained from the patient one or more autoantibodies recognizing a Thrombospondin, Type I. Domain Containing 7A (THSD7A) protein."

And should read:
-An in vitro method can diagnose membranous nephropathy in a patient. The method includes detecting in a biological sample obtained from the patient one or more autoantibodies recognizing a Thrombospondin, Type I. Domain Containing 7A (THSD7A) protein.-

Signed and Sealed this
Thirtieth Day of June, 2020

Andrei Iancu
*Director of the United States Patent and Trademark Office*